(12) United States Patent
Matsunami et al.

(10) Patent No.: US 9,739,701 B2
(45) Date of Patent: Aug. 22, 2017

(54) PARTICLE SENSOR

(71) Applicant: Panasonic Intellectual Property Management Co., Ltd., Osaka-shi, Osaka (JP)

(72) Inventors: Hirotaka Matsunami, Osaka (JP); Yoshiyuki Nakano, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/216,610

(22) Filed: Jul. 21, 2016

(65) Prior Publication Data

US 2017/0030822 A1 Feb. 2, 2017

(30) Foreign Application Priority Data

Jul. 27, 2015 (JP) ................... 2015-147792

(51) Int. Cl.
  *G01N 21/00* (2006.01)
  *G01N 15/14* (2006.01)
  (Continued)

(52) U.S. Cl.
  CPC ..... *G01N 15/1434* (2013.01); *G01N 15/0211* (2013.01); *G01N 15/1404* (2013.01);
  (Continued)

(58) Field of Classification Search
  CPC ........... G01N 33/5011; G01N 33/4833; G01N 1/2252; G01N 1/28; G01N 1/405;
  (Continued)

(56) References Cited

U.S. PATENT DOCUMENTS 6,239,710 B1 5/2001 Oppelt
2003/0223063 A1* 12/2003 Hill ..................... G01N 21/64
                                                                 356/340
(Continued)

FOREIGN PATENT DOCUMENTS

JP          2-31817 B2      3/1984
JP          59-40255 B2     9/1984
(Continued)

*Primary Examiner* — Michael P Stafira
(74) *Attorney, Agent, or Firm* — McDermott Will & Emery LLP (57) ABSTRACT

A particle sensor includes: a detecting area into which a gas including particles is introduced; a light-projecting element; a light-receiving element which receives scattered light of the light reflected by the particles in the gas in the detecting area; a heater which heats the gas; a reflector which directs the scattered light to the light-receiving element, wherein the reflector includes: a first ellipsoidal portion having an inner surface shape that defines a portion of a surface of revolution of a spheroid; and a first spherical portion having an inner surface shape that defines a portion of a spherical surface of a sphere, wherein the first ellipsoidal portion has one focus of the spheroid located in the detecting area and the other focus of the spheroid located at or proximate to the light-receiving element, and the first spherical portion has a center of the sphere located in the detecting area.

5 Claims, 4 Drawing Sheets

(51) Int. Cl.
*G01N 15/02* (2006.01)
*G01N 15/00* (2006.01)

(52) U.S. Cl.
CPC . *G01N 15/1459* (2013.01); *G01N 2015/0046* (2013.01); *G01N 2015/1486* (2013.01)

(58) Field of Classification Search
CPC ..... G01N 2001/2255; G01N 2021/495; G01N 2021/7759; G01N 2021/7786; G01N 2035/1055; G01N 21/49; G01N 21/59; G01N 21/658
See application file for complete search history.

(56) References Cited

U.S. PATENT DOCUMENTS

| | | | |
|---|---|---|---|
| 2011/0317256 A1* | 12/2011 | Hou | H01S 3/076 359/337.21 |
| 2012/0223256 A1* | 9/2012 | Bykanov | G03F 7/70925 250/504 R |
| 2014/0306115 A1* | 10/2014 | Kuritsyn | G02B 27/0006 250/358.1 |

FOREIGN PATENT DOCUMENTS

| | | | |
|---|---|---|---|
| JP | 61-160048 A | 7/1986 |
| JP | 1-37689 B2 | 8/1989 |
| JP | 4-113058 U | 10/1992 |
| JP | 6-58316 B2 | 8/1994 |
| JP | 6-58317 B2 | 8/1994 |
| JP | 7-37937 B2 | 4/1995 |
| JP | 8-201263 A | 8/1996 |
| JP | 11-248629 A | 9/1999 |
| JP | 2001-517843 A | 10/2001 |

* cited by examiner

PARTICLE SENSOR

CROSS REFERENCE TO RELATED APPLICATION

This application claims the benefit of priority of Japanese Patent Application Number 2015-147792, filed Jul. 27, 2015, the entire content of which is hereby incorporated by reference.

BACKGROUND

1. Technical Field

The present disclosure relates a particle sensor.

2. Description of the Related Art

Conventionally, a light-scattering particle sensor is known which senses airborne particles (aerosol), using light scattered by the particles.

The light-scattering particle sensor of this kind includes a light-projecting element and a light-receiving element, draws a gas to be measured, and detects presence or absence of particles in the gas using scattered light produced by the particles when the gas is irradiated by light from the light-projecting element (Japanese Unexamined Patent Application Publication No. H11-248629). Such a light-scattering particle sensor detects particles, such as airborne dust, pollen, smoke, PM 2.5 (particulates), for example.

SUMMARY

In recent years, there is a demand for further increase in efficiency of particle sensors for detecting smaller-sized fine particles. For example, it is contemplated to generate airflow using a fan, and capture a lot of particles into a particle sensor to increase the efficiency.

Installing a fan, however, increases the overall cost for a particle sensor and increases the size of the particle sensor, for example. Thus, a particle sensor with a heating mechanism using a heater such as a heater resistor (resistance heating) is proposed to achieve the size reduction and the cost reduction. The particle sensor with the heating mechanism uses the heater to cause updraft to efficiently introduce an air into the particle sensor, and detects presence or absence of particles in the air.

Specifically, as an air passes through an area (detecting area) irradiated with light from a light-projecting element, the light from the light-projecting element is reflected by particles in the air, and scattered light is produced. A light-receiving element receives the scattered light, thereby detecting the particles. In this case, for example, an air containing particles is introduced into the detecting area through a flow channel. From the standpoint of the detection efficiency of particles, preferably, the flow channel through which the air passes has an extremely small pressure drop. It is contemplated that a pressure drop in the flow channel is better be smaller, particularly, at or in proximity of the detecting area (light-scattering section). In this case, for example, the pressure drop in the channel can be reduced by increasing the cross-sectional area (bore) of the channel. However, increasing the cross-sectional area of the channel ends up increasing the size of the particle sensor.

Alternatively, it is contemplated to increase the detection efficiency of the particles by arranging a reflector (mirror), reflecting scattered light from the particles off the reflector, and collecting the scattered light onto the light-receiving element. However, the channel through which an air passes, the optical path of the light emitted from the light-projecting element, etc. need to be taken into account and it is difficult to arrange, in the vicinity of the detecting area (light-scattering section), a reflector that has a desired shape to direct the scattered light from the particles to the light-receiving element. For the reasons, even the use of a reflector does not allow conventional particle sensors to sufficiently increase the detection efficiency.

As such, the employment of a heating mechanism using a heater makes it difficult for conventional particle sensors to achieve both the size reduction and the improved efficiency.

The present disclosure is made in view of the above problem, and has an object to provide a particle sensor which achieves both size reduction and improved efficiency even though a heating mechanism using a heater is employed.

To achieve the above object, one aspect of a particle sensor according to the present disclosure includes: a detecting area into which a gas including particles is introduced; a light-projecting element which emits light to the gas in the detecting area; a light-receiving element which receives scattered light of the light reflected by the particles in the gas in the detecting area; a heater which heats the gas; a reflector which reflects and directs the scattered light to the light-receiving element, wherein: the reflector includes: a first ellipsoidal portion at least a portion of which is in an area between the detecting area and the light-receiving element, the first ellipsoidal portion having an inner surface shape that defines a portion of a surface of revolution of a spheroid; and a first spherical portion in an area on a side opposite a light-receiving element side relative to the detecting area, the first spherical portion having an inner surface shape that defines a portion of a spherical surface of a sphere, wherein the first ellipsoidal portion has a first focus, which is one of two foci of an ellipse of the spheroid of the first ellipsoidal portion, located in the detecting area, and a second focus, which is the other one of the two foci, located at or proximate to the light-receiving element, and the first spherical portion has a center of a circle of the sphere located in the detecting area.

According to the present disclosure, both size reduction and improved efficiency are readily achieved even though a particle sensor is employing a heating mechanism using a heater.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF EMBODIMENTS

Hereinafter, embodiments according to the present disclosure are described, with reference to the accompanying drawings. The embodiments described below are each merely one specific example of the present disclosure. Thus, values, shapes, materials, components, and arrangement and connection between the components shown in the following embodiments are merely by way of illustration and not intended to limit the present disclosure. Therefore, among the components in the embodiments below, components not recited in any one of the independent claims indicating the top level concept of the present disclosure are described as arbitrary components.

Figures are schematic views and do not necessarily illustrate the present disclosure precisely. In the figures, the same reference sign is used to refer to substantially the same configuration, and thus duplicate description is omitted or simplified.

X-axis, Y-axis, and Z-axis as used herein and in the figures are representation of the three axes of the three-dimensional Cartesian coordinate system, where Z-axis direction is the vertical direction, and a direction perpendicular to Z-axis (direction parallel to XY plane) is the horizontal direction.

Embodiment 1

Figure 1:
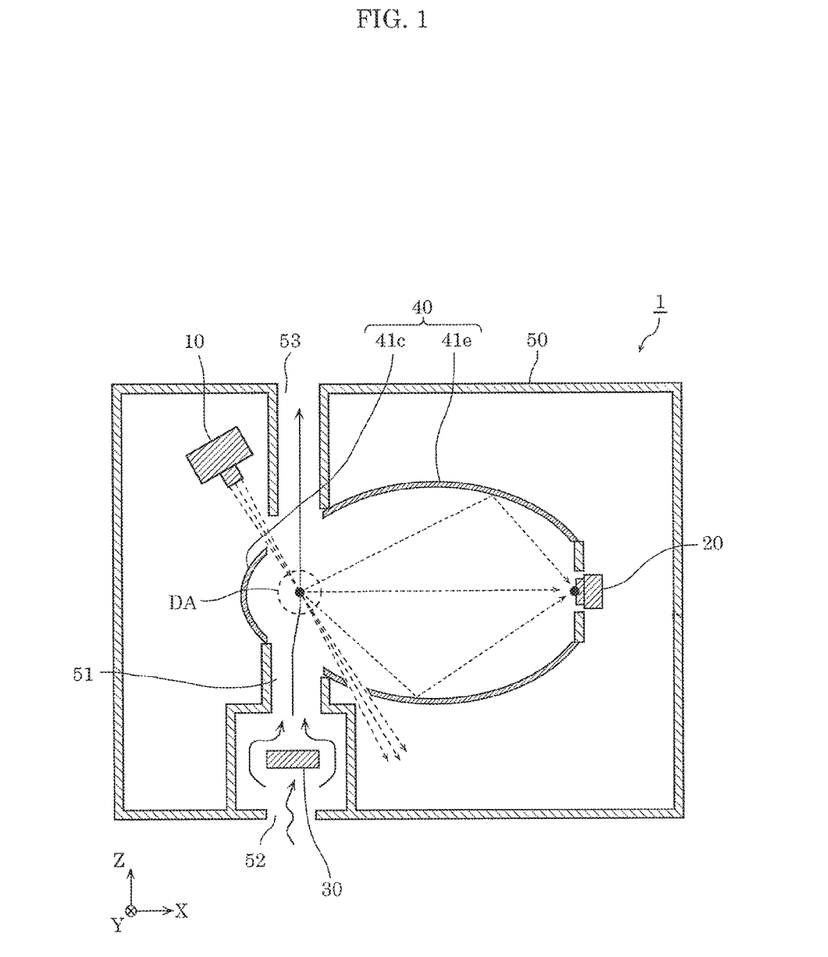
FIG. 1 is a cross-sectional view schematically showing an overall configuration of a particle sensor according to Embodiment 1.

First, particle sensor 1 according to Embodiment 1 is described, with reference to FIG. 1. FIG. 1 is a cross-sectional view schematically showing an overall configuration of particle sensor 1 according to Embodiment 1.

As shown in FIG. 1, particle sensor 1 is an optoelectronic sensor which includes light-projecting element 10 and light-receiving element 20. Particle sensor 1 detects particles in an air by receiving scattered light, using light-receiving element 20. The scattered light is light emitted by light-projecting element 10 to a gas in detecting area DA and reflected by particles in the gas in detecting area DA.

Particle sensor 1 according to the present embodiment further includes heater 30, reflector 40, and housing 50, in addition to light-projecting element 10 and light-receiving element 20. Light-projecting element 10, light-receiving element 20, heater 30, and reflector 40 are disposed within housing 50. In the present embodiment, light-projecting element 10 and light-receiving element 20 are disposed in housing 50 in a manner that the optical axis of light-projecting element 10 and the optical axis of light-receiving element 20 intersect in detecting area DA.

Detecting area DA is an aerosol detecting area (aerosol measurement section) which is an area for sensing particles (aerosol) in a gas which is a measurement subject. Detecting area DA is a light-scattering section in which light is scattered by particles in an air. In other words, in detecting area DA, the light emitted by light-projecting element 10 is reflected by particles in an air, and scattered light is produced. In the present embodiment, detecting area DA is provided in flow channel 51 in housing 50, and includes a point of intersection between the optical axis of light-projecting element 10 and the optical axis of light-receiving element 20. Detecting area DA is φ2 mm, for example.

Flow channel 51 is a gas passage which passes a gas (air, for example) introduced in housing 50 in order to measure particles in the gas. Flow channel 51 also serves a particle flow channel which passes the particles contained in the gas (air, for example), together with the gas.

Flow channel 51 is, for example, a generally cylindrical area or generally squared tubular area surrounded by the inner surface (inner wall) of housing 50, and contains detecting area DA. In the present embodiment, flow channel 51 is a straight linear flow channel extending from air intake 52 to air outtake 53. A gas to be measured is introduced from air intake 52 into flow channel 51, passes through detecting area DA and is vent out from air outtake 53.

Light-projecting element 10 is a light source (light emitter) which emits light that has a predetermined wavelength. Light-projecting element 10 is, for example, a light-emitting element which emits infrared light, blue light, green light, red light, or UV light. Light-projecting element 10 is, but not limited to, a solid-state light-emitting element such as an LED or a semiconductor laser, for example. Alternatively, light-projecting element 10 may be configured to emit light that has a mixture of two or more wavelengths. In the present embodiment, light-projecting element 10 has an optical axis that passes through detecting area DA, for example.

It should be noted that a shorter emission wavelength of light-projecting element 10 makes easier to detect small-sized particles. In addition, the scheme of controlling the light emission of light-projecting element 10 is not particularly limited. Alternatively, light emitted by light-projecting element 10 may be DC-driven into continuous light or pulsed light, for example. Alternatively, the magnitude of output of light-projecting element 10 may change over time.

Light-receiving element 20 is a light-receiving section which receives scattered light which is the light emitted by light-projecting element 10 and scattered by the particles in the gas in detecting area DA. Light-receiving element 20 is, for example, an element which receives and converts the light into an electric signal. Examples of light-receiving element 20 include a photodiode, a photo IC diode, phototransistor, and a photomultiplier.

Heater 30 heats the gas (air). Heater 30 acts as an airflow generator which generates airflow for facilitating a flow of the air in flow channel 51. In other words, heating the gas by heater 30 makes it easier to introduce the gas containing particles into detecting area DA. Heater 30 is, for example, a heater resistor available at a low cost.

In the present embodiment, heater 30 is disposed within flow channel 51. In other words, heater 30 heats the air in flow channel 51. Specifically, heater 30 is disposed vertically below detecting area DA. Accordingly, in the case where heater 30 is a heater resistor, the heater resistor produces heat as a voltage is applied to the heater resistor; the air around the heater resistor is heated and the air density decreases; and the air moves vertically upward which is opposite the gravity. In other words, as the air in flow channel 51 is heated by heater 30, vertically upward airflow (updraft) is generated.

The gas (air) to be measured can readily be drawn into housing 50 (flow channel 51) in such a manner by heater 30 heating the air in flow channel 51, thereby allowing more particles to be captured into particle sensor 1, as compared to without using heater 30. Thus, an amount of particles per unit of volume in detecting area DA included in flow channel 51 increases, thereby increasing the sensitivity in detecting area DA.

In the present embodiment, heater 30 is disposed at or proximate to air intake 52. Air intake 52, heater 30, detecting area DA, and air outtake 53 are arranged in collinear along flow channel 51.

It should be noted that the air is allowed to pass through flow channel 51 even when heater 30 is not in operation. In other words, particle sensor 1 is able to detect particles in an air even when heater 30 is not in operation.

Reflector 40 is a reflective member which reflects the scattered light which is the light emitted by light-projecting element 10 and scattered by particles in detecting area DA. Reflector 40 directs the scattered light to light-receiving element 20. In the present embodiment, reflector 40 is a collecting mirror which reflects and collects onto light-receiving element 20 the scattered light from the particles in detecting area DA.

Reflector 40 includes first ellipsoidal portion (first ellipsoidal area) 41e and first spherical portion (first spherical area) 41c. First ellipsoidal portion 41e is a primary reflective member (first reflective member) of reflector 40. First spherical portion 41c is an auxiliary reflective member (second reflective member) of reflector 40.

First ellipsoidal portion 41e is disposed in an area between detecting area DA and light-receiving element 20. Specifically, first ellipsoidal portion 41e is disposed between flow channel 51 and a light-receiving surface of light-receiving element 20.

Furthermore, first ellipsoidal portion 41e has an inner surface shape that defines a portion of a surface of revolution of a spheroid. In other words, first ellipsoidal portion 41e is an ellipsoidal mirror an inner surface (reflective surface) of which has a shape that defines a shape of the portion of the spheroid, and a cross-sectional shape of the inner surface of first ellipsoidal portion 41e defines a portion of an ellipse.

First ellipsoidal portion 41e has an opening which opens toward flow channel 51 so that the scattered light from detecting area DA can be incident on reflector 40. Specifically, the opening of first ellipsoidal portion 41e opens toward detecting area DA. It should be noted that flow channel 51 has a first opening corresponding to the opening of first ellipsoidal portion 41e. The first opening of flow channel 51 has a size substantially the same as a size of the opening of first ellipsoidal portion 41e.

At least a portion of first spherical portion 41c is disposed in an area on a side opposite a light-receiving element 20 side relative to detecting area DA. In the present embodiment, the entirety of first spherical portion 41c is disposed in the area on the side opposite the light-receiving element 20 side relative to detecting area DA. Stated differently, using detecting area DA (light-scattering section) as a point of origin of the coordinate system, some or the entirety of first spherical portion 41c is 90 degrees or greater anticlockwise away from light-receiving element 20 about the origin.

Specifically, first spherical portion 41c is disposed such that flow channel 51 is located between first spherical portion 41c and first ellipsoidal portion 41e. First spherical portion 41c is disposed so that the inner surface of which is facing the light-receiving surface of light-receiving element 20.

Furthermore, first spherical portion 41c has an inner surface shape that defines a portion of a spherical surface of a sphere. In other words, first spherical portion 41c is a spherical mirror an inner surface (reflective surface) of which has a shape that defines a shape of the portion of the spherical surface, and a cross-sectional shape of the inner surface of first spherical portion 41c defines a portion of a circle.

First spherical portion 41c has an opening which opens toward flow channel 51 so that the scattered light from detecting area DA can be incident on reflector 40. Specifically, the opening of first spherical portion 41c opens toward detecting area DA. It should be noted that flow channel 51 has a second opening corresponding to the opening of first spherical portion 41c. The second opening of flow channel 51 needs to allow the light emitted from light-projecting element 10 to pass therethrough. Thus, the second opening of flow channel 51 has a size greater than a size of the opening of first spherical portion 41c.

The inner surface of reflector 40 (first ellipsoidal portion 41e, first spherical portion 41c) is a reflective surface. For example, the inner surface of reflector 40 may be a surface which less likely to cause scattered light and is a surface (mirrored surface, for example) that has low absorption and high reflectivity. This can direct a great amount of light incident on reflector 40 to light-receiving element 20. Reflector 40 may include a base member made of a metal or the like so that the inner surface itself can be a reflective surface. Alternatively, reflector 40 may include a resin or metal base member whose inner surface has a reflective film formed thereon acting as a reflective surface. Examples of the reflective film include metal reflective films made of aluminum, gold, silver, copper, etc., a specular reflective film, and a dielectric multilayer.

Housing 50 is a case which accommodates light-projecting element 10, light-receiving element 20, heater 30, and reflector 40. Specifically, housing 50 is such configured that it can hold light-projecting element 10, light-receiving element 20, heater 30, and reflector 40. Housing 50 is a flat rectangular parallelepiped, box-shaped resin case, for example.

Housing 50 has air intake 52 for introducing the air into flow channel 51, and air outtake 53 for venting the air out of flow channel 51.

Air intake 52 is an air feed (air inlet) for supplying a gas such as an air present external to particle sensor 1 into the interior (flow channel 51) of particle sensor 1. Air intake 52 is an entrance for an air into housing 50.

Air outtake 53, on the other hand, is an air vent (air outlet) for venting the air in the interior (flow channel 51) of particle sensor 1 out of particle sensor 1. Air outtake 53 is an exit for the air out of housing 50.

Air intake 52 is in communication with one end of flow channel 51 and air outtake 53 is in communication with the other end of flow channel 51. This introduces an air (gas to be measured) containing particles into housing 50 from air intake 52, permits the air to flow into detecting area DA through flow channel 51, and vents the air out of housing 50 from air outtake 53. It should be noted that configuring the open area of air intake 52 to be greater than the open area of air outtake 53 allows the air to be more efficiently introduced into and exhausted out of housing 50.

Figure 2:
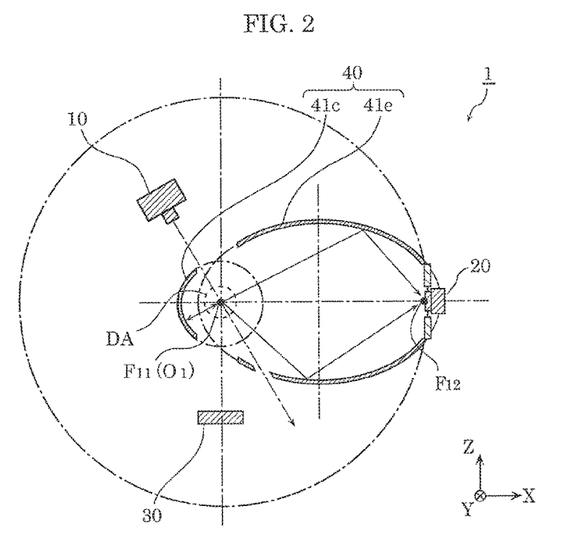
FIG. 2 is a diagram for illustrating optics of the particle sensor according to Embodiment 1 in XZ plane.
Figure 3:
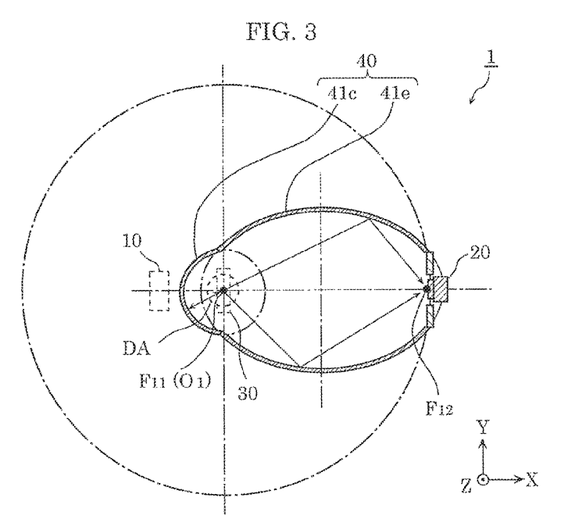
FIG. 3 is a diagram for illustrating the optics of the particle sensor according to Embodiment 1 in XY plane.

Next, referring to FIG. 1, the positional relationship between and the optical actions of light-projecting element 10, light-receiving element 20, reflector 40, and detecting area DA in particle sensor 1 according to the present embodiment are described in detail, with reference to FIGS. 2 and 3. FIG. 2 is a diagram for illustrating optics of particle sensor 1 according to Embodiment 1 in XZ plane. FIG. 3 is a diagram for illustrating the optics of particle sensor 1 in XY plane. Specifically, FIGS. 2 and 3 show light-projecting element 10, light-receiving element 20, reflector 40, and detecting area DA as optics of particle sensor 1.

As shown in FIGS. 2 and 3, first ellipsoidal portion 41e of reflector 40 is an ellipsoidal mirror and configured of a spheroid. First ellipsoidal portion 41e has focus $F_{11}$ (first focus), which is one of two foci $F_{11}$ and $F_{12}$ of an ellipse of the spheroid, located in detecting area DA and focus $F_{12}$ (second focus), which is the other of the two foci $F_{11}$ and $F_{12}$, located at or proximate to light-receiving element 20. In other words, detecting area DA is configured so as to include focus $F_{11}$ of the ellipse of first ellipsoidal portion 41e, and light-receiving element 20 is disposed at or proximate to focus $F_{12}$ of the ellipse of first ellipsoidal portion 41e.

Placing focus $F_{11}$ of the ellipse of the inner surface of first ellipsoidal portion 41e in relation to detecting area DA and placing focus $F_{12}$ of the ellipse in relation to light-receiving element 20 as such allow light traveling to the light-receiving element 20 side (light traveling to an area on the right side relative to detecting area DA in FIGS. 2 and 3), among the scattered light from the particles in detecting area DA, to reflect off first ellipsoidal portion 41e and be incident on light-receiving element 20.

Moreover, as shown in FIGS. 2 and 3, first spherical portion 41c of reflector 40 is a spherical mirror formed of a sphere. First spherical portion 41c has center $O_1$ (center of the sphere) of a circle of the sphere located in detecting area DA. In the present embodiment, center $O_1$ of the circle in first spherical portion 41c and focus $F_{11}$ (first focus) of the ellipse in first ellipsoidal portion 41e coincide with each other. Center $O_1$ of the circle in first spherical portion 41c also coincides with the center of detecting area DA.

Placing center $O_1$ of first spherical portion 41c in relation to detecting area DA as such allows light that is traveling to a side (the light traveling to an area on the left side relative to detecting area DA in FIGS. 2 and 3) opposite the light-receiving element 20 side to reflect off first spherical portion 41c back to detecting area DA provided in relation to focus $F_{11}$ of the ellipse in first ellipsoidal portion 41e, among the scattered light from the particles in detecting area DA. Since detecting area DA includes focus $F_{11}$ of the ellipse of first ellipsoidal portion 41e, the light returned to detecting area DA passes through detecting area DA, reflects off first ellipsoidal portion 41e, and is incident on light-receiving element 20 disposed in relation to focus $F_{12}$.

In the present embodiment, the circle of first spherical portion 41c encompasses detecting area DA. In other words, the diameter of the circle of first spherical portion 41c is greater than the diameter of detecting area DA. Furthermore, preferably, the diameter of the circle of first spherical portion 41c is greater than the length of the major axis of the ellipse of first ellipsoidal portion 41e minus a focus-to-focus distance (distance between focus $F_{11}$ and focus $F_{12}$).

As shown in FIG. 1, the light emitted by light-projecting element 10 is focused on detecting area DA. In the present embodiment, the light emitted by light-projecting element 10 is focused at focus $F_{11}$. For example, by disposing an optical member (projection lens, for example) in front of light-projecting element 10, the light (projected beam) emitted by light-projecting element 10 is allowed to be focused on detecting area DA (focus $F_{11}$). For example, a collecting lens configured of, for example, a transparent resin lens or a glass lens may be disposed in front of light-projecting element 10. In this case, a focal point of the light which exits the collecting lens coincides with focus $F_{11}$. Alternatively, rather than a collecting lens, a collimating lens may be disposed in front of light-projecting element 10. In this case, light which exits the collimating lens may be focused at focus $F_{11}$, using an aperture.

Making the focal point of the light emitted by light-projecting element 10 coincide with focus $F_{11}$ of the ellipse of first ellipsoidal portion 41e as such allows for a great density of the light, thereby increasing the amount of light that is scattered by the particles in detecting area DA. Thus, the detection efficiency of particles is further increased.

Particle sensor 1 configured as described above detects particles as follows, for example.

As an air is drawn from air intake 52 into particle sensor 1 (housing 50), the air is directed to detecting area DA via flow channel 51 in housing 50.

In this case, if the air contains particles (aerosol), the light emitted by light-projecting element 10 is scattered by the particles in detecting area DA. A portion of the scattered light from the particles is reflected by reflector 40 and directed to light-receiving element 20. As the light is incident on light-receiving element 20, a predetermined signal is output from light-receiving element 20, and thus presence of the particles in the air introduced in particle sensor 1 can be seen.

Moreover, sizes of the particles (particle sizes) can be determined from the magnitude of the signal output by light-receiving element 20, that is, the magnitude of the light intensity of the scattered light from the particles. Thus, whether the particles in the air are dust, pollen, smoke, or PM 2.5 (particulates) can be determined.

Furthermore, since each one of the signal outputs by light-receiving element 20, that is, each one of peaks of the light intensity of the scattered light from the particles corresponds to each one of the particles, the number (amount) of particles in the air introduced in particle sensor 1 can be calculated as well.

On the other hand, if the air introduced in particle sensor 1 contains no particle, no particle flows into detecting area DA. As a result, the light emitted by light-projecting element 10 passes straight through detecting area DA, and no scattered light is produced. Consequently, in this case, light-receiving element 20 basically shows no response and thus it can be seen that there is no particle in the air introduced in particle sensor 1.

Figure 4:
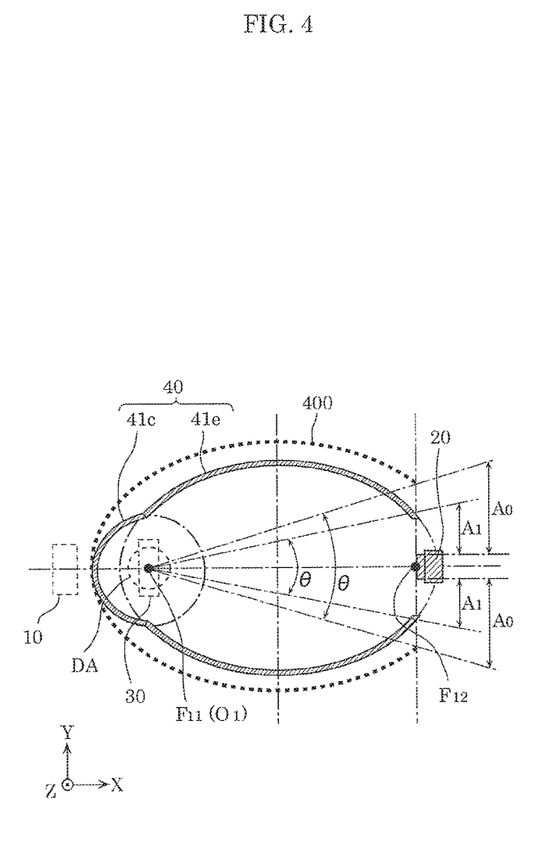
FIG. 4 is a diagram for illustrating effects of a reflector included in the particle sensor according to Embodiment 1.

Next, effects of reflector 40 included in particle sensor 1 according to the present embodiment are described, with reference to FIG. 4. FIG. 4 is a diagram for illustrating effects of reflector 40 included in particle sensor 1 according to Embodiment 1.

In the present embodiment, reflector 40 is disposed in the area between detecting area DA and light-receiving element 20 and includes first ellipsoidal portion 41e having an inner surface shape that defines a portion of a surface of revolution of a spheroid. This allows, as described above, light traveling to the light-receiving element 20 side, among the scattered light from the particles in detecting area DA, to be reflected by first ellipsoidal portion 41e and incident on light-receiving element 20. In other words, use of first ellipsoidal portion 41e whose reflective surface is an ellipsoidal surface allows causing the scattered light from the particles in detecting area DA to be reflected a small number of times (once or a few times) and incident on light-receiving element 20. This can prevent the light from being reflected multiple times and attenuated, thereby increasing the light reception efficiency in light-receiving element 20. As a result, the detection efficiency of particles increases.

It has also been contemplated to incorporate a reflector, such as an ellipsoidal mirror, into conventional particle sensors to have the reflector reflect the light scattered by particles in detecting area DA (light-scattering section), and have a light-receiving element receive the reflected light. In this case, conventional reflector 400 is, as indicated by the dotted line in FIG. 4, an ellipsoidal mirror in which reflector 400 has an overall ellipsoidal shape.

Thus, if light-receiving element 20 is disposed close to detecting area DA for the purpose of size reduction, as shown in FIG. 4, area (null area) $A_0$ results where the light scattered by the particles in detecting area DA is not incident on light-receiving element 20. Consequently, the detection efficiency of particles decreases. It should be noted that the null area is defined by straight lines between the center of detecting area DA and the open end of reflector 400 on the light-receiving element 20 side. A range of the null area is represented by null angle θ.

In particle sensor 1 according to the present embodiment, in contrast, an outline of the ellipse of first ellipsoidal portion 41e of reflector 40 is smaller than an outline of the ellipse of reflector 400 indicated by the dotted line. This allows narrowing down area (null area) $A_1$ where the light scattered by the particles in detecting area DA is not incident on light-receiving element 20, as compared to using reflector 400. In other words, this reduces null angle θ.

In this case, simply reducing analogously the overall outline of the entire ellipse of reflector 400 ends up reducing the cross-sectional area (bore) of flow channel 51 in detecting area DA as much as the outline is reduced. This precludes the capability of arranging reflector 400 having a reduced outline in the vicinity of detecting area DA, or, even if reflector 400 is able to be arranged, increases the pressure drop in flow channel 51, ending up decreasing the detection efficiency.

In particle sensor 1 according to the present embodiment, in contrast, reflector 40 is disposed in an area on the side opposite the light-receiving element 20 side relative to detecting area DA, and includes first spherical portion 41c having the inner surface shape that defines a portion of the spherical surface of the sphere.

According to this, even though reflector 40 (first spherical portion 41c) is disposed in the vicinity of detecting area DA, the cross-sectional area (bore) of flow channel 51 in the vicinity of detecting area DA can be increased as compared to disposing reflector 400 having an overall ellipsoidal shape. Thus, the pressure drop in flow channel 51 is inhibited, thereby increasing the detection efficiency of particles.

Moreover, first spherical portion 41c has center $O_1$ of the circle of the sphere located in detecting area DA.

This allows the light traveling to the side opposite the light-receiving element 20 side to be reflected by first spherical portion 41c back to detecting area DA, among the scattered light from the particles in the detecting area DA. Then the light reflected by first spherical portion 41c back to detecting area DA (focus $F_{11}$) and the light traveling to the light-receiving element 20 side, among the scattered light from the particles in detecting area DA, are reflected by first ellipsoidal portion 41e and incident on light-receiving element 20 disposed in relation to focus $F_{12}$.

Providing not only first ellipsoidal portion 41e but also first spherical portion 41c as such allows the light traveling to the side opposite the light-receiving element 20 side, among the scattered light from the particles in the detecting area DA, to be efficiently captured into light-receiving element 20. Thus, the light reception efficiency in light-receiving element 20 further increases, thereby further increasing the detection efficiency of particles.

As described above, according to particle sensor 1 of the present embodiment, reflector 40 includes first ellipsoidal portion 41e and first spherical portion 41c. This increases the detection efficiency of particles, while narrowing down null area $A_1$ located at or proximate to light-receiving element 20 even though a heating mechanism in which the air is introduced into detecting area DA by heater 30 is employed and the entire size of the sensor is reduced. In other words, both the size reduction and the improved efficiency are readily achieved even though a particle sensor is employing a heating mechanism using heater 30.

In the present embodiment, the diameter of the circle in first spherical portion 41c may be greater than the long diameter of the ellipse in first ellipsoidal portion 41e minus the focus-to-focus distance.

This allows size reduction of the entirety of reflector 40, without changing the size of reflector 40 in the vicinity of detecting area DA (light-scattering section).

In the present embodiment, center $O_1$ of the circle in first spherical portion 41c and focus $F_{11}$ (first focus) of the ellipse in first ellipsoidal portion 41e coincide with each other.

This allows the light having reflected off first spherical portion 41c back to detecting area DA (focus $F_{11}$) to be reflected by first ellipsoidal portion 41e and incident on light-receiving element 20 (focus $F_{12}$), by making the center of detecting area DA coincide with focus $F_{12}$ (second focus) of the ellipse of first ellipsoidal portion 41e. In other words, this allows light reflected off first spherical portion 41c to be efficiently incident on light-receiving element 20. Thus, the light reception efficiency in light-receiving element 20 increases, thereby further increasing the detection efficiency of particles.

Embodiment 2

Figure 5:
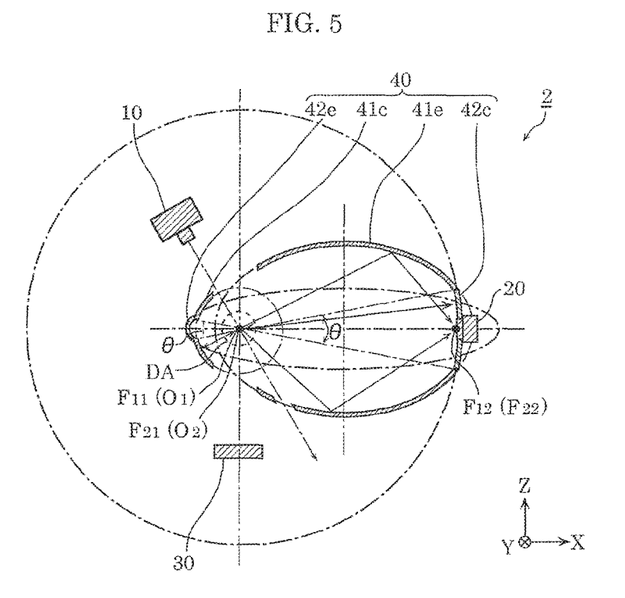
FIG. 5 is a diagram for illustrating optics of a particle sensor according to Embodiment 2 in XZ plane.
Figure 6:
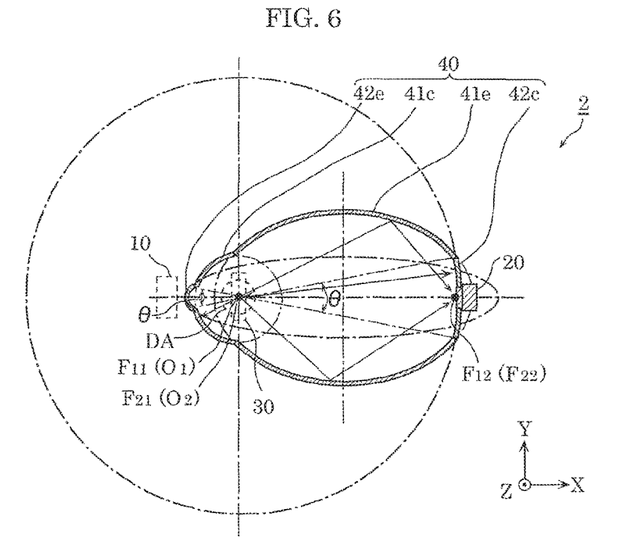
FIG. 6 is a diagram for illustrating the optics of the particle sensor according to Embodiment 2 in XY plane.

Next, particle sensor 2 according to Embodiment 2 is described, with reference to FIGS. 5 and 6. FIG. 5 is a diagram for illustrating optics of particle sensor 2 according to Embodiment 2 in XZ plane. FIG. 6 is a diagram for illustrating the optics of particle sensor 2 in XY plane.

As shown in FIGS. 5 and 6, particle sensor 2 according to the present embodiment has the same configuration as particle sensor 1 according to Embodiment 1, except that reflector 40 included in particle sensor 2 further includes second spherical portion (second spherical area) 42c and second ellipsoidal portion (second ellipsoidal area) 42e.

In the present embodiment, second spherical portion 42c and second ellipsoidal portion 42e are auxiliary reflective members included in reflector 40.

At least a portion of second spherical portion 42c is disposed in an area on a side opposite a detecting area DA side relative to focus $F_{12}$ (second focus) of an ellipse of first ellipsoidal portion 41e. In the present embodiment, the entirety of second spherical portion 42c is disposed in an area on the side opposite the detecting area DA side relative to focus $F_{12}$. In other words, in FIGS. 5 and 6, second spherical portion 42c is disposed in an area on the right side relative to focus $F_{12}$ (second focus). Stated differently, using light-receiving element 20 as a point of origin of the coordinate system, some or the entirety of second spherical portion 42c is 90 degrees or greater anticlockwise away from detecting area DA about the origin.

Specifically, second spherical portion 42c is disposed between light-receiving element 20 and the edge of first ellipsoidal portion 41e on the light-receiving element 20 side, and connected to light-receiving element 20 and the edge of first ellipsoidal portion 41e on the light-receiving element 20 side. In other words, second spherical portion 42c is disposed in null area $A_1$ in FIG. 4.

Second spherical portion 42c is disposed facing first spherical portion 41c via detecting area DA, and has an inner surface facing an inner surface of first spherical portion 41c.

Second spherical portion 42c has an inner surface shape that defines a portion of a spherical surface of a sphere. Second spherical portion 42c has center $O_2$ (the center of the sphere) of a circle of the sphere located in detecting area DA. In the present embodiment, center $O_2$ of the circle of second spherical portion 42c coincides with the center of detecting area DA. That is to say, center $O_2$ of the circle of second spherical portion 42c coincides also with center $O_1$ of the circle of first spherical portion 41c. Thus, the circle of second spherical portion 42c and the circle of first spherical portion 41c are concentric. In the present embodiment, the diameter of the circle of second spherical portion 42c is greater than the diameter of the circle of first spherical portion 41c. It should be noted that center $O_2$ of the circle of second spherical portion 42c also coincides with focus $F_{11}$ of the ellipse of first ellipsoidal portion 41e.

Second ellipsoidal portion 42e is disposed in an area on a side opposite the light-receiving element 20 side relative to detecting area DA. In other words, in FIGS. 5 and 6, second ellipsoidal portion 42e is disposed in an area on the left side relative to detecting area DA.

Second ellipsoidal portion 42e is provided continuing with first spherical portion 41c at a portion of first spherical portion 41c. Specifically, second ellipsoidal portion 42e is provided in the range of null angle θ in first spherical portion 41c.

Second ellipsoidal portion 42e has an inner surface shape that defines a portion of the surface of revolution of a spheroid. Second ellipsoidal portion 42e has focus $F_{21}$ (first focus), which is one of two foci $F_{21}$ and $F_{22}$ of an ellipse of the spheroid of second ellipsoidal portion 42e, located in detecting area DA and focus $F_{22}$ (second focus), which is the other of the two foci $F_{21}$ and $F_{22}$, located at or proximate to light-receiving element 20.

In the present embodiment, the two foci (focus $F_{21}$, focus $F_{22}$) of the ellipse of second ellipsoidal portion 42e coincide with the two foci (focus $F_{11}$, focus $F_{12}$) of the ellipse of first ellipsoidal portion 41e. Specifically, focus $_{21}$ (first focus) of the ellipse of second ellipsoidal portion 42e and focus $F_{11}$ (first focus) of the ellipse of first ellipsoidal portion 41e coincide with each other, and focus $F_{22}$ (second focus) of the ellipse of second ellipsoidal portion 42e and focus $F_{12}$ (second focus) of first ellipsoidal portion 41e coincide with each other. In other words, focus $F_{21}$ of the ellipse of second ellipsoidal portion 42e is in relation to detecting area DA, and focus $F_{22}$ of the ellipse of second ellipsoidal portion 42e is in relation to light-receiving element 20. Thus, the ellipse of second ellipsoidal portion 42e and the ellipse of first ellipsoidal portion 41e are analogous to each other. In the present embodiment, the length of the major axis (minor axis) of the ellipse of second ellipsoidal portion 42e is greater than the length of the major axis (minor axis) of the ellipse of first ellipsoidal portion 41e.

Next, effects of reflector 40 included in particle sensor 2 according to the present embodiment are described.

As described above, in the present embodiment, second spherical portion 42c, which has center $O_2$ in relation to detecting area DA, and second ellipsoidal portion 42e, which has two foci $F_{21}$ and $F_{22}$ respectively in relation to detecting area DA and light-receiving element 20, are disposed in this manner. This allows light scattered by the particles and incident on null area $A_1$ in FIG. 4 to be captured into light-receiving element 20 as well.

In other words, the light incident on second spherical portion 42c, among scattered light from the particles in detecting area DA, reflects off second spherical portion 42c back to detecting area DA. The light having returned to detecting area DA from second spherical portion 42c passes through detecting area DA and is incident on second ellipsoidal portion 42e. The light incident on second ellipsoidal portion 42e from second spherical portion 42c is reflected by second ellipsoidal portion 42e and directly incident on light-receiving element 20 disposed in relation to focus $F_{22}$. In this manner, the light scattered by the particles and incident on null area $A_1$ in FIG. 4 can also be captured into light-receiving element 20 by further providing second spherical portion 42c and second ellipsoidal portion 42e. This further increases the light reception efficiency in light-receiving element 20, thereby further increasing the detection efficiency of particles.

Among the scattered light from the particles in the detecting area DA, the light traveling to the side opposite the light-receiving element 20 side is reflected by first spherical portion 41c, further reflected by first ellipsoidal portion 41e, and then incident on light-receiving element 20 in Embodiment 1. In the present embodiment, in contrast, among the light traveling to the side opposite the light-receiving element 20 side, light incident on and reflected by second ellipsoidal portion 42e is directly incident on light-receiving element 20, without being reflected by first ellipsoidal portion 41e. This inhibits attenuation of light due to reflections, thereby further increasing the light reception efficiency in light-receiving element 20 and further increasing the detection efficiency of particles.

As described above, according to particle sensor 2 of the present embodiment, reflector 40 includes second spherical portion 42c and second ellipsoidal portion 42e, in addition to first ellipsoidal portion 41e and first spherical portion 41c. This achieves a further increase of the detection efficiency of particles as compared to particle sensor 1 according to Embodiment 1. Thus, a particle sensor that achieves both the size reduction and the improved efficiency is further readily implemented.

Variation

While the particle sensor according to the present disclosure has been described, with reference to the embodiments, the present disclosure is not limited to the above embodiments.

For example, in Embodiments 1 and 2 described above, first ellipsoidal portion 41e and first spherical portion 41c may be formed in one piece or may be separate components. While first ellipsoidal portion 41e and first spherical portion 41c are continuously formed as shown in FIGS. 3 and 6, first ellipsoidal portion 41e and first spherical portion 41c may be disposed spaced apart from each other.

Alternatively, in Embodiments 1 and 2 described above, a light trap (labyrinth) may be provided to absorb stray light in housing 50. The light trap allows a further increase of the sensing efficiency of particles. For example, a light trap may be provided facing light-projecting element 10 to prevent, among the light emitted by light-projecting element 10, light that has passed through detecting area DA, without hitting particles in detecting area DA, from being reflected and scattered in housing 50 and received by light-receiving element 20. In other instances, a light trap may be provided in housing 50 as appropriate. The light trap is, for example, a closed space defined by a structure (wedge structure, etc) in which light entered the light trap is reflected multiple times and attenuated.

In Embodiments 1 and 2 described above, desirably, first ellipsoidal portion 41e and second ellipsoidal portion 42e are spheroids, in particular, flat-plate spheroids. However, taking the moldability into account, first ellipsoidal portion 41e and second ellipsoidal portion 42e may each have a certain cross-sectional shape being ellipse.

The particle sensor according to Embodiments 1 to 2 described above can be incorporated into a dust sensor. For example, when the particle sensor built in a dust sensor senses dust particles, the dust sensor signals the detection of dust by sound or light or display.

The particle sensor according to Embodiments 1 and 2 described above can be incorporated into a smoke detector. For example, if the particle sensor built in a smoke detector senses smoke particles, the smoke detector signals the detection of smoke by sound or light or display.

The particle sensor according to Embodiments 1 and 2 described above or the dust sensor can be incorporated into an air cleaner, ventilating fan, or air conditioner, for example. In this case, for example, if the particle sensor built in an air cleaner, ventilating fan, or air conditioner senses dust particles, the air cleaner, ventilating fan, or air conditioner may simply display the detection of dust on a display or may control a fan such as activation of the fan or changing a fan speed.

In other instances, various modifications to the embodiments according to the present disclosure described above that may be conceived by a person skilled in the art and embodiments implemented by any combination of the components and functions shown in the above embodiments are also included within the scope of the present disclosure, without departing from the spirit of the present disclosure.

What is claimed is:

1. A particle sensor comprising:
    a detecting area into which a gas including particles is introduced;
    a light-projecting element which emits light to the gas in the detecting area;
    a light-receiving element which receives scattered light of the light reflected by the particles in the gas in the detecting area;
    a heater which heats the gas;
    a reflector which reflects and directs the scattered light to the light-receiving element, wherein:
    the reflector includes:
        a first ellipsoidal portion at least a portion of which is in an area between the detecting area and the light-receiving element, the first ellipsoidal portion having an inner surface shape that defines a portion of a surface of revolution of a spheroid; and
        a first spherical portion in an area on a side opposite a light-receiving element side relative to the detecting area, the first spherical portion having an inner surface shape that defines a portion of a spherical surface of a sphere,
    the first ellipsoidal portion has a first focus, which is one of two foci of an ellipse of the spheroid of the first ellipsoidal portion, located in the detecting area, and a second focus, which is the other one of the two foci, located at or proximate to the light-receiving element, and
    the first spherical portion has a center of a circle of the sphere located in the detecting area.

2. The particle sensor according to claim 1, wherein a diameter of the circle is greater than a major diameter of the ellipse minus a focus-to-focus distance.

3. The particle sensor according to claim 1, wherein the center of the circle of the first spherical portion and the first focus of the ellipse of the first ellipsoidal portion coincide with each other.

4. The particle sensor according to claim 1, wherein:
    the reflector further includes:
    a second spherical portion at least a portion of which is in an area on a side opposite a detecting area side relative to the second focus, the second spherical portion having an inner surface shape that defines a portion of a spherical surface of a sphere;
    a second ellipsoidal portion in an area on the side opposite the light-receiving element side relative to the detecting area, the second ellipsoidal portion having an inner surface shape that defines a portion of a surface of revolution of a spheroid,
    the second spherical portion has a center of a circle of the sphere of the second spherical portion located in the detecting area, and
    the second ellipsoidal portion has a first focus, which is one of two foci of an ellipse of the spheroid of the second ellipsoidal portion, located in the detecting area, and a second focus, which is the other one of the two foci of the second ellipsoidal portion, located at or proximate to the light-receiving element.

5. The particle sensor according to claim 4, wherein:
    the first focus of the ellipse of the second ellipsoidal portion and the first focus of the ellipse of the first ellipsoidal portion coincide with each other, and
    the second focus of the ellipse of the second ellipsoidal portion and the second focus of the ellipse of the first ellipsoidal portion coincide with each other.

* * * * *